United States Patent
Marshall et al.

(10) Patent No.: US 12,376,899 B2
(45) Date of Patent: Aug. 5, 2025

(54) TISSUE RESECTING DEVICE INCLUDING A BLADE LOCK AND RELEASE MECHANISM

(71) Applicant: Covidien LP, Mansfield, MA (US)

(72) Inventors: Peter F. Marshall, Bolton, MA (US); Timothy J. Wood, Wilmington, MA (US)

(73) Assignee: Covidien LP, Mansfield, MA (US)

( * ) Notice: Subject to any disclaimer, the term of this patent is extended or adjusted under 35 U.S.C. 154(b) by 227 days.

(21) Appl. No.: 17/537,715

(22) Filed: Nov. 30, 2021

(65) Prior Publication Data

US 2022/0079665 A1    Mar. 17, 2022

Related U.S. Application Data (63) Continuation of application No. 16/171,479, filed on Oct. 26, 2018, now Pat. No. 11,197,710.

(51) Int. Cl.
*A61B 18/14* (2006.01)
*A61B 17/32* (2006.01)
(Continued)

(52) U.S. Cl.
CPC .... *A61B 18/1445* (2013.01); *A61B 17/32002* (2013.01); *A61B 2017/00477* (2013.01); *A61B 2018/00922* (2013.01)

(58) Field of Classification Search
CPC ............ A61B 18/149; A61B 17/32002; A61B 17/320016; A61B 2017/0046; A61B 2018/00208

See application file for complete search history.

(56) References Cited

U.S. PATENT DOCUMENTS

| 1,585,934 A | 5/1926 | Muir |
| 1,666,332 A | 4/1928 | Hirsch |
| (Continued) | | |

FOREIGN PATENT DOCUMENTS

| DE | 3206381 A1 | 9/1983 |
| DE | 3339322 A1 | 5/1984 |
| (Continued) | | |

OTHER PUBLICATIONS

Extended European Search Repo5b4rt issued in corresponding European Application No. 19205301.5 dated Jan. 31, 2020, 9 pages.

(Continued)

*Primary Examiner* — Anh T Dang
(74) *Attorney, Agent, or Firm* — Carter, DeLuca & Farrell LLP (57) ABSTRACT

An end effector assembly of a tissue resecting device and a tissue resecting device including the end effector assembly and a handpiece assembly. The end effector assembly including a proximal hub housing, an inner drive core at least partially disposed within the proximal hub housing, a cutting member extending distally from the proximal hub housing and engaged with the inner drive core such that rotation of the inner drive core rotates the cutting member, and a lock and release mechanism operably coupled between the inner drive core and the proximal hub housing. The lock and release mechanism is transitionable between a locked condition rotationally fixing the inner drive core and the proximal hub housing relative to one another thereby rotationally locking the cutting member, and a release condition enabling relative rotation between the inner drive core and the proximal hub housing thereby enabling rotation of the cutting member.

10 Claims, 7 Drawing Sheets

(51) Int. Cl.
*A61B 17/00* (2006.01)
*A61B 18/00* (2006.01)

(56) References Cited

U.S. PATENT DOCUMENTS

| | | |
|---|---|---|
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,971,034 A | 11/1990 | Doi et al. |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,586,973 A | 12/1996 | Lemaire et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |

(56) References Cited

U.S. PATENT DOCUMENTS

| | | |
|---|---|---|
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,025,656 B2 | 9/2011 | Gruber et al. |
| 8,061,359 B2 | 11/2011 | Emanuel |
| 8,062,214 B2 | 11/2011 | Shener et al. |
| 8,419,626 B2 | 4/2013 | Shener-Irmakoglu et al. |
| 8,465,421 B2 | 6/2013 | Finkman et al. |
| 8,528,563 B2 | 9/2013 | Gruber |
| 8,574,253 B2 | 11/2013 | Gruber et al. |
| 8,647,349 B2 | 2/2014 | Gruber et al. |
| 8,663,264 B2 | 3/2014 | Cesarini et al. |
| 8,678,999 B2 | 3/2014 | Isaacson |
| 8,834,487 B2 | 9/2014 | Gruber et al. |
| 8,840,625 B2 | 9/2014 | Adams et al. |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,760 B2 | 6/2015 | Sullivan et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,095,366 B2 | 8/2015 | Sullivan et al. |
| 9,125,550 B2 | 9/2015 | Shener-Irmakoglu et al. |
| 9,155,454 B2 | 10/2015 | Sahney et al. |
| 9,259,233 B2 | 2/2016 | Gruber et al. |
| 11,197,710 B2 | 12/2021 | Marshall et al. |
| 2008/0058842 A1 | 3/2008 | Emanuel |
| 2008/0097468 A1 | 4/2008 | Adams |
| 2008/0097469 A1 | 4/2008 | Gruber |
| 2008/0097470 A1 | 4/2008 | Gruber |
| 2008/0097471 A1 | 4/2008 | Adams |
| 2008/0135053 A1 | 6/2008 | Gruber |
| 2008/0146872 A1 | 6/2008 | Gruber |
| 2008/0146873 A1 | 6/2008 | Adams |
| 2008/0245371 A1 | 10/2008 | Gruber |
| 2008/0249366 A1 | 10/2008 | Gruber |
| 2008/0249534 A1 | 10/2008 | Gruber |
| 2008/0249553 A1 | 10/2008 | Gruber |
| 2008/0262308 A1 | 10/2008 | Prestezog |
| 2009/0082628 A1 | 3/2009 | Kucklick |
| 2009/0270812 A1 | 10/2009 | Litscher |
| 2009/0270895 A1 | 10/2009 | Churchill |
| 2009/0270896 A1 | 10/2009 | Sullivan |
| 2009/0270897 A1 | 10/2009 | Adams |
| 2009/0270898 A1 | 10/2009 | Chin |
| 2010/0087798 A1 | 4/2010 | Adams |
| 2010/0152647 A1 | 6/2010 | Shener |
| 2011/0034943 A1 | 2/2011 | Churchill |
| 2011/0077674 A1 | 3/2011 | Sullivan et al. |
| 2011/0118544 A1 | 5/2011 | Adams |
| 2011/0166419 A1 | 7/2011 | Reif |
| 2012/0067352 A1 | 3/2012 | Gruber |
| 2012/0078038 A1 | 3/2012 | Sahney et al. |
| 2013/0131452 A1 | 5/2013 | Kuroda |
| 2014/0003183 A1 | 1/2014 | Song |
| 2014/0277036 A1 | 9/2014 | Flynn et al. |

FOREIGN PATENT DOCUMENTS

| | | |
|---|---|---|
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |
| DE | 19751632 C1 | 9/1999 |
| DE | 102006022827 A1 | 12/2006 |
| EP | 0310285 A2 | 4/1989 |
| EP | 0327410 A1 | 8/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 11/1997 |
| EP | 1681022 A1 | 7/2006 |
| GB | 2093353 A | 9/1982 |
| GB | 2311468 A | 10/1997 |
| JP | 2001075416 A | 3/2001 |
| JP | 2002529185 A | 9/2002 |
| JP | 2002538889 A | 11/2002 |
| JP | 2003245247 A | 9/2003 |
| NL | 1006944 C2 | 3/1999 |
| WO | 20198101648 A1 | 6/1981 |
| WO | 9211816 A2 | 7/1992 |
| WO | 20199307821 | 4/1993 |
| WO | 20199315664 | 8/1993 |
| WO | 20199426181 | 11/1994 |
| WO | 20199510981 | 4/1995 |

(56) References Cited

FOREIGN PATENT DOCUMENTS

| | | |
|---|---|---|
| WO | 20199510982 | 4/1995 |
| WO | 20199522935 | 8/1995 |
| WO | 20199530377 | 11/1995 |
| WO | 20199611638 | 4/1996 |
| WO | 20199626676 | 9/1996 |
| WO | 20199709922 | 3/1997 |
| WO | 20199717027 | 5/1997 |
| WO | 20199719642 | 6/1997 |
| WO | 20199724071 | 7/1997 |
| WO | 20199734534 | 9/1997 |
| WO | 20199735522 | 10/1997 |
| WO | 9810707 | 3/1998 |
| WO | 20199809569 | 3/1998 |
| WO | 20199846147 | 10/1998 |
| WO | 20199903407 | 1/1999 |
| WO | 20199903409 | 1/1999 |
| WO | 20199907295 | 2/1999 |
| WO | 20199911184 | 3/1999 |
| WO | 20199939648 | 8/1999 |
| WO | 20199944506 | 9/1999 |
| WO | 20199960935 | 12/1999 |
| WO | 0012010 A1 | 3/2000 |
| WO | 0028890 A1 | 5/2000 |
| WO | 0033743 A1 | 6/2000 |
| WO | 0044295 A1 | 8/2000 |
| WO | 0047116 A1 | 8/2000 |
| WO | 0057797 A1 | 10/2000 |
| WO | 0135831 A1 | 5/2001 |
| WO | 0158368 A1 | 8/2001 |
| WO | 0195810 A2 | 12/2001 |
| WO | 0234147 A1 | 5/2002 |
| WO | 02069808 A2 | 9/2002 |
| WO | 03022164 A1 | 3/2003 |
| WO | 03077767 A1 | 9/2003 |
| WO | 2005060842 A1 | 7/2005 |
| WO | 2005096963 A2 | 10/2005 |
| WO | 2006105283 A2 | 10/2006 |
| WO | 2006121968 A2 | 11/2006 |
| WO | 2006121970 A2 | 11/2006 |
| WO | 2007044833 A2 | 4/2007 |
| WO | 2012044705 A1 | 4/2012 |
| WO | 2016205197 A1 | 12/2016 |

OTHER PUBLICATIONS

Extended European Search Report issued in corresponding European Application No. 23183010.0 dated Sep. 20, 2023, 8 pages.

TISSUE RESECTING DEVICE INCLUDING A BLADE LOCK AND RELEASE MECHANISM

CROSS-REFERENCE TO RELATED APPLICATIONS

This application is a continuation of U.S. patent application Ser. No. 16/171,479, filed on Oct. 16, 2018, the entire contents of which are hereby incorporated herein by reference.

BACKGROUND

1. Technical Field

The present disclosure relates generally to the field of tissue resection. In particular, the present disclosure relates to a tissue resecting device including a blade lock and release mechanism.

2. Background of Related Art

Tissue resection may be performed endoscopically within an organ, such as a uterus, by inserting an endoscope (or hysteroscope) into the uterus and passing a tissue resection device through the endoscope (or hysteroscope) and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space.

SUMMARY

As used herein, the term "distal" refers to the portion that is described which is further from a user, while the term "proximal" refers to the portion that is described which is closer to a user. Further, to the extent consistent, any or all of the aspects described herein may be used in conjunction with any or all of the other aspects described herein.

Provided in accordance with aspects of the present disclosure is an end effector assembly of a tissue resecting device. The end effector assembly includes a proximal hub housing, an inner drive core at least partially disposed within the proximal hub housing, and a cutting member extending distally from the proximal hub housing and engaged with the inner drive core such that rotation of the inner drive core rotates the cutting member. The end effector assembly further includes a lock and release mechanism operably coupled between the inner drive core and the proximal hub housing. The lock and release mechanism is transitionable between a locked condition rotationally fixing the inner drive core and the proximal hub housing relative to one another thereby rotationally locking the cutting member, and a release condition enabling relative rotation between the inner drive core and the proximal hub housing thereby enabling rotation of the cutting member.

In an aspect of the present disclosure, the lock and release mechanism is biased towards the locked condition.

In another aspect of the present disclosure, the end effector assembly further includes an elongated outer shaft fixed relative to and extending distally from the proximal hub housing. The cutting member is received within the elongated outer shaft, rotationally fixed relative to the elongated outer shaft in the locked condition, and rotatable relative to the elongated outer shaft in the release condition.

In still another aspect of the present disclosure, the elongated outer shaft defines an outer window and the cutting member defines a cutting blade. In the locked condition, the cutting blade is inaccessible through the outer window.

In yet another aspect of the present disclosure, the lock and release mechanism includes a first portion and a second portion rotationally fixed relative to the first portion. In the in the locked condition, the first portion is rotationally fixed relative to the inner drive core and the second portion is rotationally fixed relative to the proximal hub housing. In the release condition, the first portion is rotatable relative to the inner drive core or the second portion is rotatable relative to the proximal hub housing.

In still yet another aspect of the present disclosure, the first portion includes a first stop ring and the second portion includes a second stop ring. The first stop ring or the second stop ring is movable relative to the other to transition the lock and release mechanism between the locked condition and the release condition.

In another aspect of the present disclosure, the lock and release mechanism further includes a biasing member disposed between the first and second stop rings and configured to bias the lock and release mechanism towards the locked condition.

In yet another aspect of the present disclosure, the first stop ring, the second stop ring, and the biasing member are integrally formed as a single piece.

In still another aspect of the preset disclosure, the lock and release mechanism includes a lock bar rotationally fixed relative to the inner drive core. The lock bar includes a first portion pivotable between a first position, corresponding to the locked condition, wherein the first portion engages the proximal hub housing in rotationally fixed relation, and a second position, corresponding to the release condition, wherein the first portion is disengaged from the proximal hub housing.

A tissue resecting device provided in accordance with aspects of the present disclosure includes a handpiece assembly including a drive rotor and an end effector assembly according to any of the above aspects or other aspects detailed herein. Engagement of the end effector assembly with the handpiece operably engages the drive rotor with the inner drive core and transitions the lock and release mechanism from the locked condition to the release condition.

In an aspect of the present disclosure, engagement of the end effector assembly with the handpiece urges a portion of the handpiece into contact with one of a first portion or a second portion of the lock and release mechanism, thereby decoupling fixed rotation of the first portion relative to the inner drive core or decoupling fixed rotation of the second portion relative to the proximal hub housing.

In another aspect of the present disclosure, a first portion of the lock and release mechanism includes a first stop ring and a second portion includes a second stop ring. In such aspects, engagement of the end effector assembly with the handpiece urges the first stop ring relative to the second stop ring, thereby decoupling the first stop ring from fixed relation relative to the inner drive core.

In yet another aspect of the present disclosure, the lock and release mechanism further includes a biasing member disposed between the first and second stop rings and configured to bias the first stop ring towards a position establishing fixed rotational relation between the first stop ring and the inner drive core.

In still another aspect of the present disclosure, the lock and release mechanism includes a lock bar rotationally fixed relative to the inner drive core. The lock bar includes a first portion pivotable between a first position, corresponding to the locked condition, wherein the first portion engages the proximal hub housing in rotationally fixed relation, and a second position, corresponding to the release condition, wherein the first portion is disengaged from the proximal hub housing.

In still yet another aspect of the present disclosure, the lock bar includes a second portion. In such aspects, engagement of the end effector assembly with the handpiece urges a portion of the handpiece into contact with the second portion to pivot the second portion, thereby pivoting the first portion to disengage the first portion from the proximal hub housing.

A method of assembling a tissue resection device for use provided in accordance with aspects of the present disclosure includes obtaining an end effector assembly including a proximal hub housing, a inner drive core, a cutting member engaged with the inner drive core, and a lock and release mechanism disposed in a locked condition rotationally fixing the inner drive core and the proximal hub housing relative to one another thereby rotationally locking the cutting member. The method further includes engaging the end effector assembly with a handpiece assembly including a drive rotor and a handle housing. Engaging the end effector assembly with the handpiece includes engaging the proximal hub housing with the handle housing, engaging the drive rotor with the inner drive core, and transitioning the lock and release mechanism to a release position enabling relative rotation between the inner drive core and the proximal hub housing thereby enabling rotation of the cutting member.

In an aspect of the present disclosure, engaging the drive rotor with the inner drive core includes engaging splines of the drive rotor with splines of the inner drive core.

In another aspect of the present disclosure, transitioning the lock and release mechanism to the release position includes urging a stop ring into contact with a portion of the handle housing to move the stop ring from an engaged position to a disengaged position.

In another aspect of the present disclosure, transitioning the lock and release mechanism to the release position includes urging a first portion of a lock bar into contact with a cam surface of the drive rotor to pivot a second portion of the lock bar from an engaged position to a disengaged position.

BRIEF DESCRIPTION OF THE DRAWINGS

Various aspects and features of the present disclosure are described hereinbelow with reference to the drawings wherein like numerals designate identical or corresponding elements in each of the several views and.

DETAILED DESCRIPTION

Figure 1:
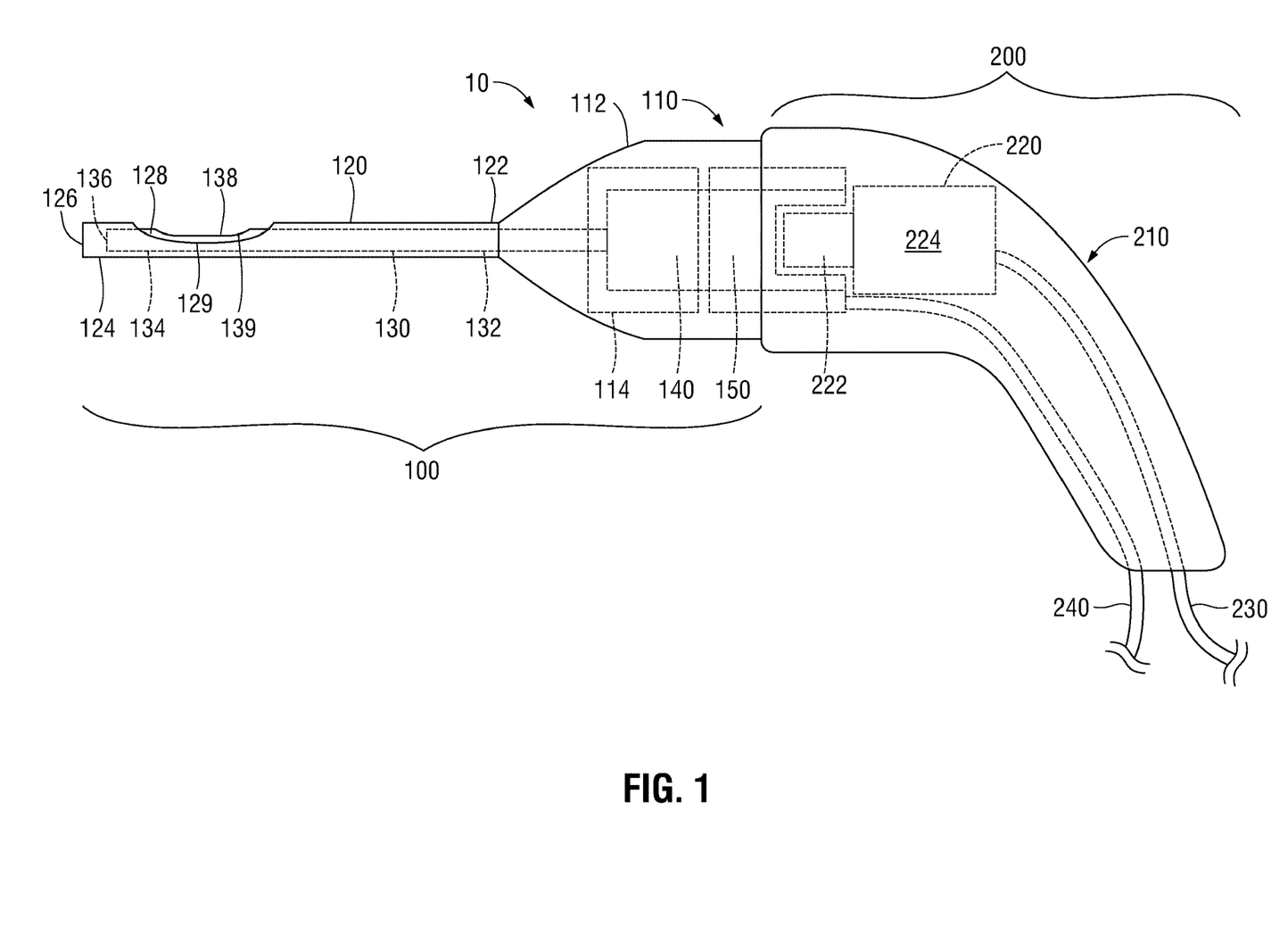
FIG. 1 is a side view of a tissue resecting device provide in accordance with aspects of the present disclosure.

Referring generally to FIG. 1, a tissue resecting device 10 provided in accordance with the present disclosure and configured to resect tissue includes an end effector assembly 100 and a handpiece assembly 200. Tissue resecting device 10 is adapted to connect to a control unit (not shown), e.g., via cable 230, to provide power and control functionality to tissue resecting device 10, although tissue resecting device 10 may alternatively or additionally include controls associated with handpiece assembly 200 and/or a power source, e.g., battery, disposed within handpiece assembly 200. In other embodiments, tissue resecting device 10 is manually powered and/or controlled. Tissue resecting device 10 is further adapted to connect to a fluid management system (not shown), e.g., via outflow tubing 240, for removing fluid, tissue, and debris from a surgical site via tissue resecting device 10. The control unit and fluid management system may be integral with one another, coupled to one another, or separate from one another.

With continued reference to FIG. 1, tissue resecting device 10 may be configured as a single-use device that is discarded after use or sent to a manufacturer for reprocessing, a reusable device capable of being cleaned and/or sterilized for repeated use by the end-user, or a partially-single-use, partially-reusable device. With respect to partially-single-use, partially-reusable configurations, handpiece assembly 200 may be configured as a cleanable/sterilizable, reusable component, while end effector assembly 100 is configured as a single-use, disposable/reprocessable component. In either of the above configurations, end effector assembly 100 is configured to releasably engage handpiece assembly 200 to facilitate disposal/reprocessing of any single-use components and cleaning and/or sterilization of any reusable components. Further, enabling releasable engagement of end effector assembly 100 with handpiece assembly 200 allows for use of different end effector assemblies with handpiece assembly 200.

End effector assembly 100 includes a proximal hub housing 110, an elongated outer shaft 120 fixedly engaged with and extending distally from proximal hub housing 110, an inner cutting shaft 130 movable disposed within elongated outer shaft 120, and an inner drive core 140, and a lock and release mechanism 150. Inner drive core 140 is operably disposed within proximal hub housing 110 and coupled to inner cutting shaft 130 such that rotational input imparted to inner drive core 140, e.g., via handpiece assembly 200, drives rotation of inner cutting shaft 130 within and relative to elongated outer shaft 120. In embodiments, inner cutting shaft 130 may be configured to additionally or alternatively reciprocate relative to elongated outer shaft 120. Lock and release mechanism 150, as detailed below, is configured to selectively lock and release inner drive core 140, thereby selectively locking and releasing inner cutting shaft 130.

Figure 3:
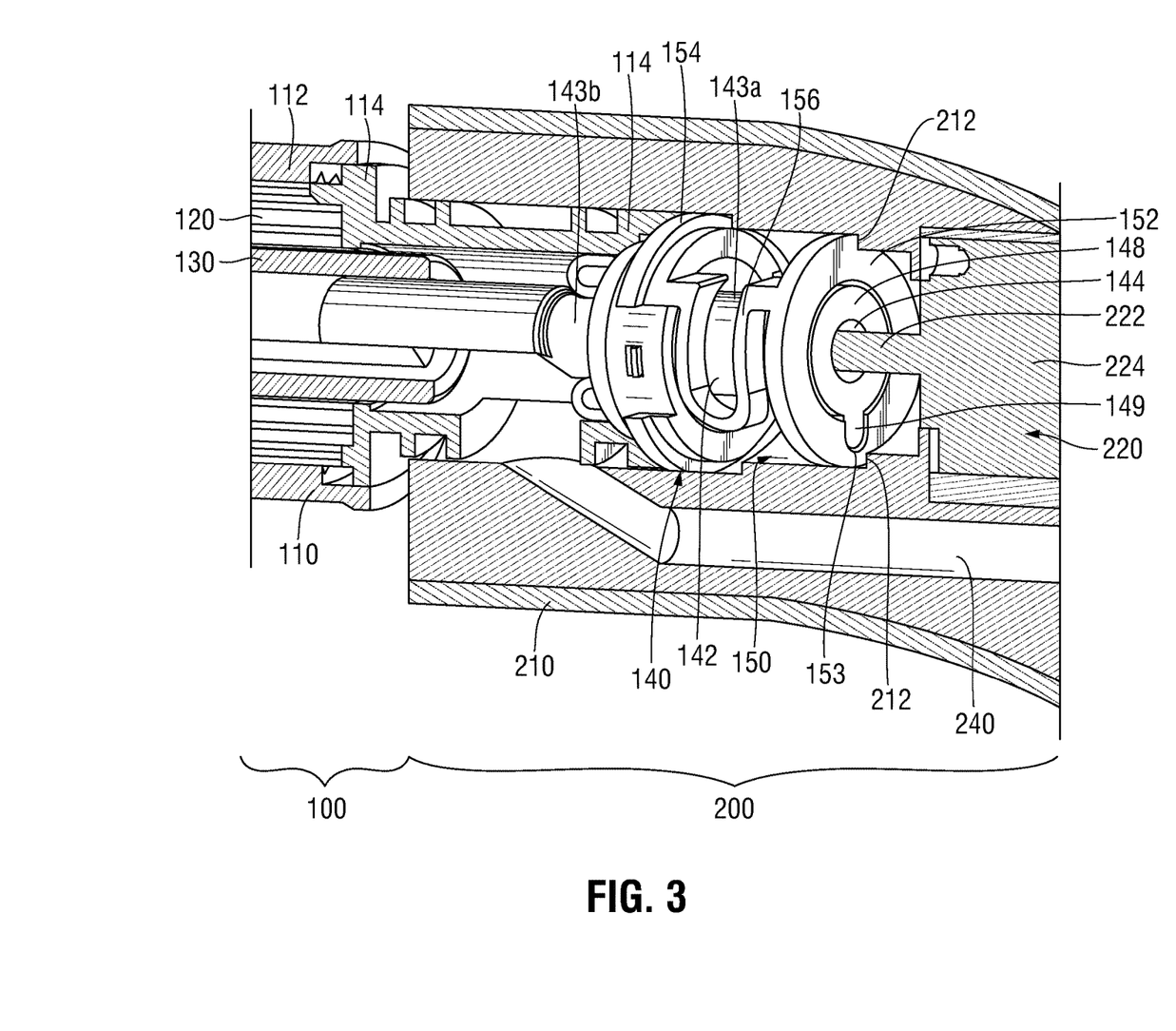
FIG. 3 is a longitudinal, cross-sectional view of a portion of the tissue resecting device of FIG. 1 illustrating the end effector assembly partially inserted into a handpiece assembly of the tissue resecting device with a lock and release mechanism of the end effector assembly disposed in a locked condition.
Figure 4:
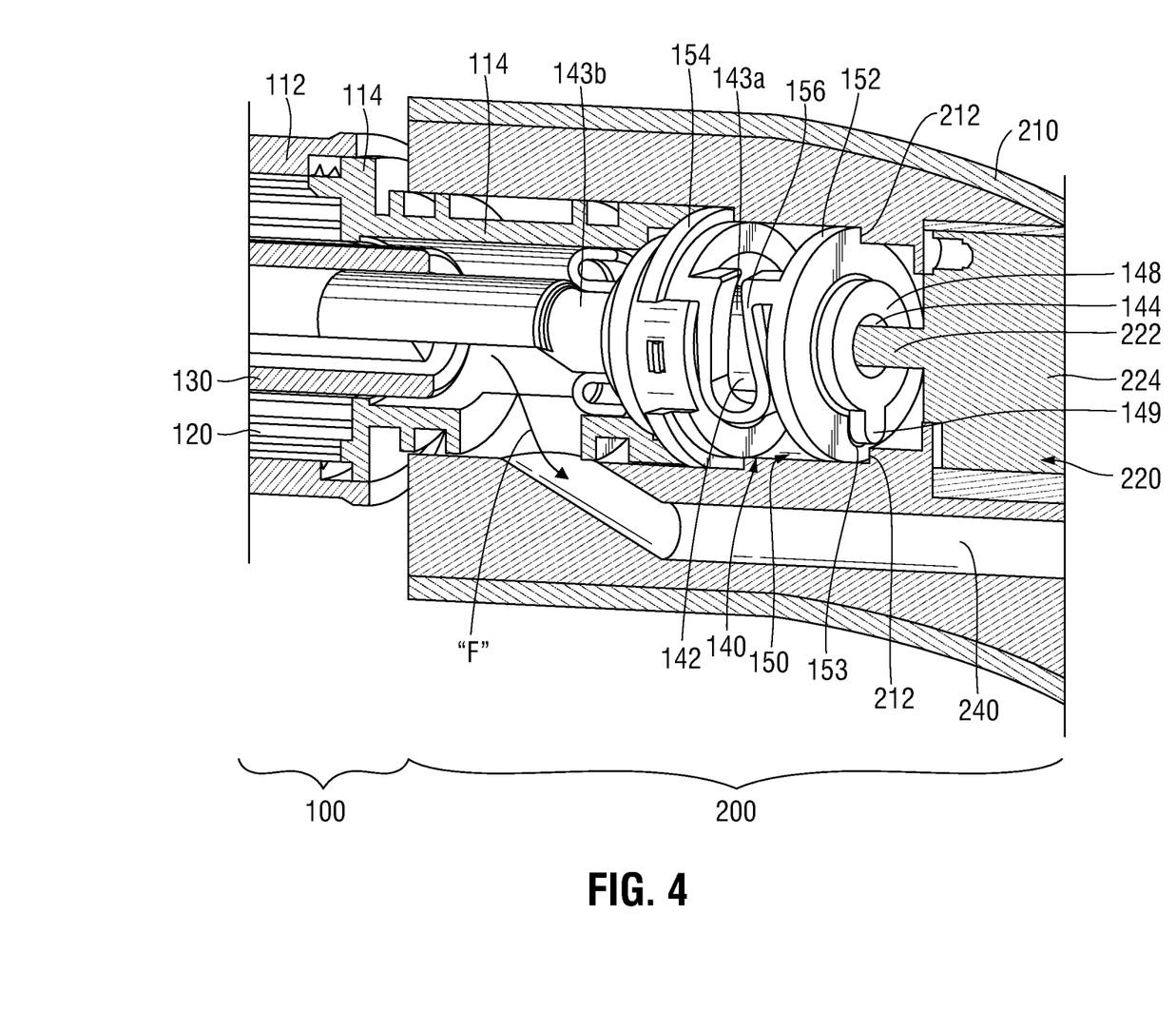
FIG. 4 is a longitudinal, cross-sectional view of a portion of the tissue resecting device of FIG. 1 illustrating the end effector assembly engaged with the handpiece assembly with the lock and release mechanism disposed in a release condition.

Proximal hub housing 110 of end effector assembly 100 includes an outer housing 112 and an inner housing 114 disposed in fixed orientation relative to one another, e.g., fixedly engaged with one another. In embodiments, as illustrated in FIGS. 3 and 4, a distal end portion of inner housing 114 is disposed within and engaged to a proximal portion of outer housing 112 with inner housing 114 extending proximally from outer housing 112, although other configurations are also contemplated. Regardless of the particular configuration of outer housing 112 and inner housing 114, outer housing 112 and/or inner housing 114 is configured to releasably engage handle housing 210 of handpiece assembly 200, e.g., via snap-fit, threaded, luer-lock, lock-button, or other suitable engagement, and may be configured for fixed engagement with handle housing 210 or rotational engagement therewith.

Figure 2A:
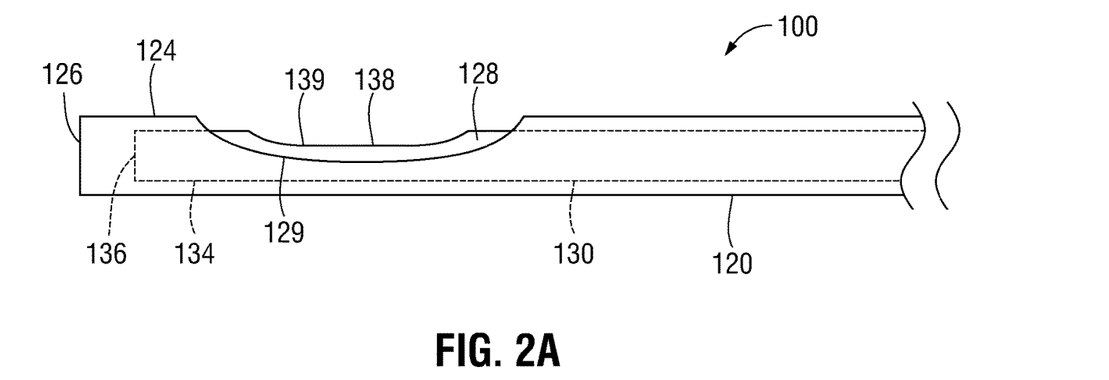
FIG. 2A is a side view of an end effector assembly of the tissue resecting device of FIG. 1, disposed in an open position.
Figure 2B:
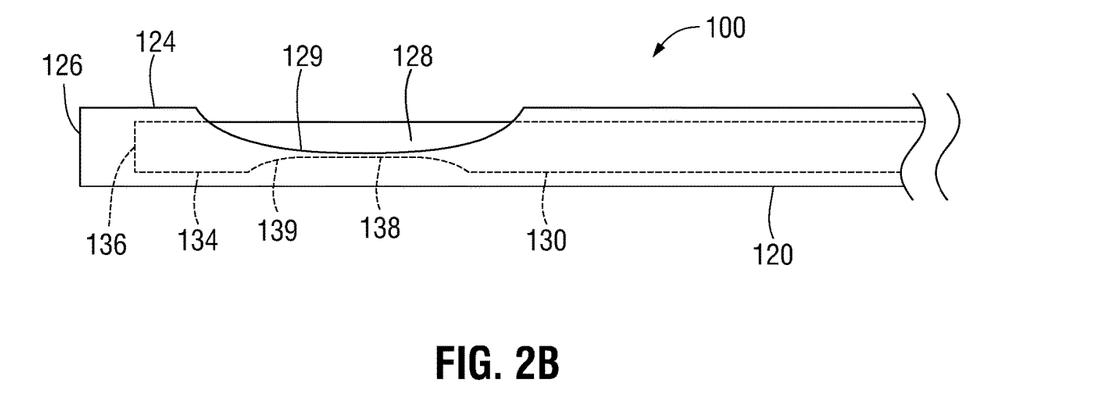
FIG. 2B is a side view of the end effector assembly of the tissue resecting device of FIG. 1, disposed in a closed position.

Elongated outer shaft 120 of end effector assembly 100 includes a proximal end portion 122 extending into and fixedly engaged within proximal hub housing 110, e.g., engaged with outer or inner housing 112, 114, respectively. With additional reference to FIGS. 2A and 2B, elongated outer shaft 120 extends distally from proximal hub housing 110 to distal end portion 124 defining a closed distal end 126 and a window 128 proximally-spaced from closed distal end 126. Window 128 provides access to the interior of elongated outer shaft 120 and may be surrounded by a cutting edge 129 about the outer perimeter of window 128 so as to facilitate cutting of tissue passing through window 128 and into elongated outer shaft 120. Alternatively, edge 129 may be blunt.

Inner cutting shaft 130 includes a proximal end portion 132 and a distal end portion 134 defining a closed distal end 136 and a window 138 proximally-spaced from closed distal end 136. The edge of inner cutting shaft 130 surrounding window 138 defines a cutting blade 139 to facilitate cutting of tissue passing through window 138 and into inner cutting shaft 130. Inner cutting shaft 130 is rotatable relative to elongated outer shaft 120. Inner cutting shaft 130 may be continuously rotated in a single direction or may be configured to reverse and move in opposite directions. In either configuration, rotation of inner cutting shaft 130 relative to elongated outer shaft 120 defines at least one open position of end effector assembly 100 (see FIG. 2A), wherein inner cutting shaft 130 is oriented relative to elongated outer shaft 120 such that window 138 at least partially overlaps window 128, thus enabling fluid communication therebetween, and at least one closed position of end effector assembly 100 (see FIG. 2B), wherein inner cutting shaft 130 is oriented relative to elongated outer shaft 120 such that window 138 does not radially overlap window 128, thus inhibiting fluid communication therebetween. In the at least one open position, cutting blade 139 is exposed; in the at least one closed position, cutting blade 139 is not exposed. As detailed below, lock and release mechanism 150 is configured to lock inner cutting shaft 130 in a closed position, e.g., the position illustrated in FIG. 2B, prior to engagement of end effector assembly 100 with handpiece assembly 200 and to release cutting shaft 130 once end effector assembly 100 is engaged with handpiece assembly 200.

Referring to FIGS. 1, 3, 5A, and 6A, inner drive core 140 of end effector assembly 100 includes a generally cylindrical body 142 defining a lumen 144 extending longitudinally therethrough. Body 142 includes a proximal portion 143a and a distal portion 143b. Proximal portion 143a of body 142 includes a plurality of splines 146 radially-spaced about the interior of body 142 and, thus, radially surrounding a proximal portion of lumen 144. Proximal portion 143a of body 142 extends proximally from proximal hub housing 110 of end effector assembly 100. Distal portion 143b of body 142 extends distally through inner housing 114 of proximal hub housing 110 and is (directly or indirectly) fixedly engaged with proximal end portion 132 of inner cutting shaft 130 (see FIG. 3) within inner housing 114. As such, rotation of body 142 imparts rotation to inner cutting shaft 130. Inner drive core 140 further includes a collar 148 disposed about a proximal portion of body 142 and fixed relative thereto. Collar 148 includes a protrusion 149 extending radially outwardly therefrom.

Continuing with reference to FIGS. 1, 3, 5A, and 6A, lock and release mechanism 150 of end effector assembly 100 includes a proximal stop ring 152, a distal stop ring 154 rotationally fixed relative to proximal stop ring 152, and a biasing member 156 disposed between proximal and distal stop rings 152, 154, respectively. Proximal stop ring 152 defines a recess 153 and, in an at-rest position of biasing member 156, is radially disposed about collar 148 of inner drive core 140 with protrusion 149 of collar 148 received within recess 153, thus rotatably fixing inner drive core 140 relative to proximal stop ring 152. Distal stop ring 154 is fixed relative to inner housing 114 of proximal hub housing 110, e.g., via molding, adhering, compression-fitting, seating, etc. distal stop ring 154 over or within a proximal portion of inner housing 114, although other suitable methods or manners of fixing distal stop ring 154 relative to inner housing 114 of proximal hub housing 110 are also contemplated.

Biasing member 156 may be a living hinge formed integrally with proximal and distal stop rings 152, 154, respectively, e.g., formed as a single molded component, although biasing member 156 may alternatively be formed separately from either or both of proximal and distal stop rings 152, 154, respectively, and/or may be any other suitable biasing member such as, for example, a compression spring. Biasing member 156 is configured to bias proximal stop ring 152 relative to distal stop ring 154 towards an at-rest position wherein, as noted above, proximal stop ring 152 is radially disposed about collar 148 of inner drive core 140 with protrusion 149 of collar 148 received within recess 153, thus rotatably fixing inner drive core 140 relative to proximal stop ring 152. In embodiments, the protrusion and recess may be reversed, e.g., where the protrusion extends from proximal stop ring 152 and the recesses is defined within collar 148.

As detailed above, the receipt of protrusion 149 of collar 148 within recess 153 of proximal stop ring 152 in the at-rest position of biasing member 156 rotatably fixes inner drive core 140 and, thus, inner cutting shaft 130, relative to proximal stop ring 152. Further, as also detailed above, proximal and distal stop rings 152, 154, respectively, are rotationally fixed relative to one another, and distal stop ring 154 is rotationally fixed relative to inner housing 114 of proximal hub housing 110 and, thus, elongated outer shaft 120. Thus, in the at-rest position of biasing member 156, inner cutting shaft 130 is locked relative to elongated outer shaft 120. In embodiments, protrusion 149 and recess 153 are oriented such that inner cutting shaft 130 is locked in a closed position relative to elongated outer shaft 120, e.g., wherein window 138 does not radially overlap window 128, thus inhibiting fluid communication therebetween, and wherein cutting blade 139 is not exposed.

Figure 5A:
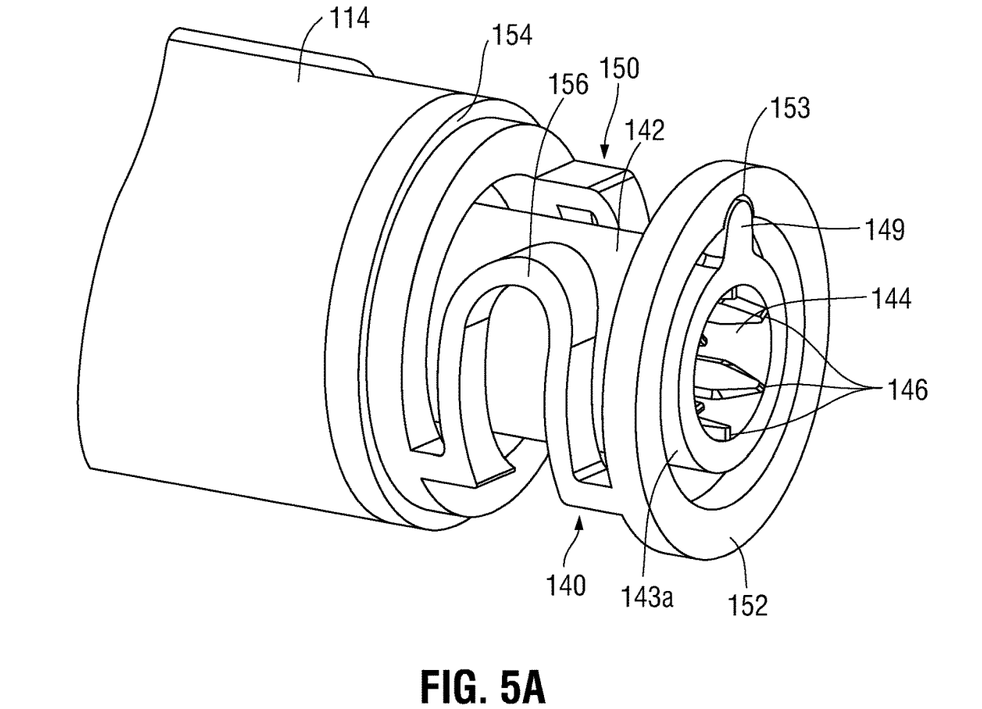
FIG. 5A is a perspective view of a proximal portion of the end effector assembly of the tissue resecting device of FIG. 1 illustrating the lock and release mechanism in the locked condition.
Figure 5B:
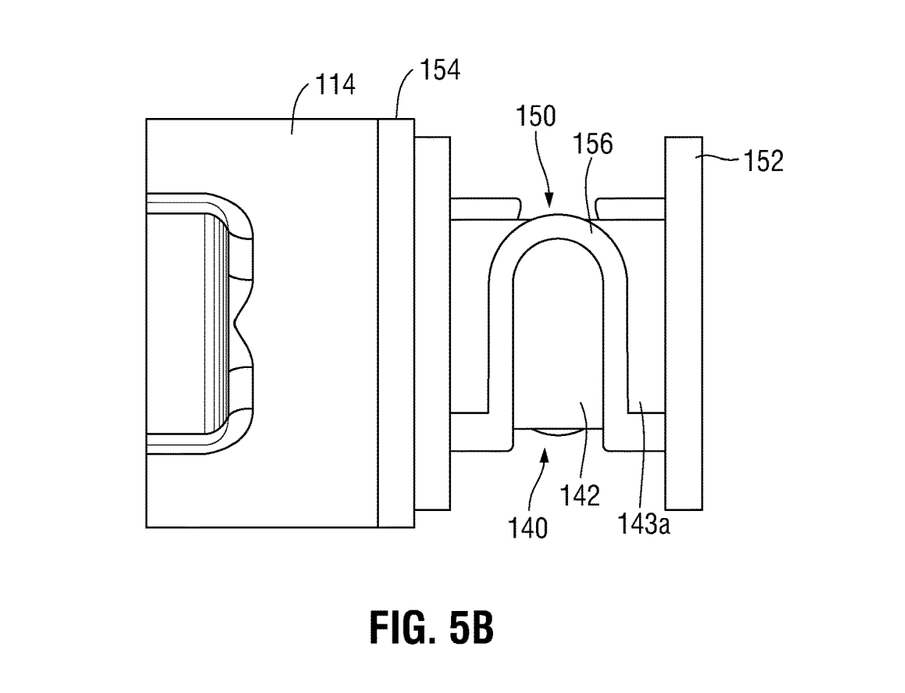
FIG. 5B is a side view of a proximal portion of the end effector assembly of the tissue resecting device of FIG. 1 illustrating the lock and release mechanism in the locked condition.
Figure 6A:
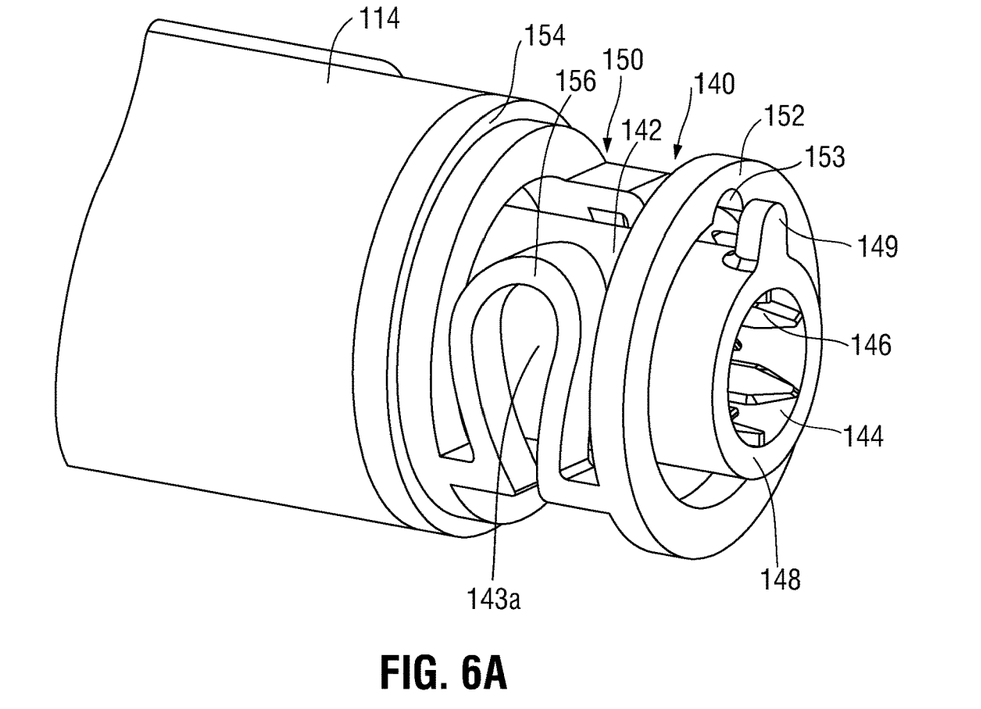
FIG. 6A is a perspective view of a proximal portion of the end effector assembly of the tissue resecting device of FIG. 1 illustrating the lock and release mechanism in the release condition.
Figure 6B:
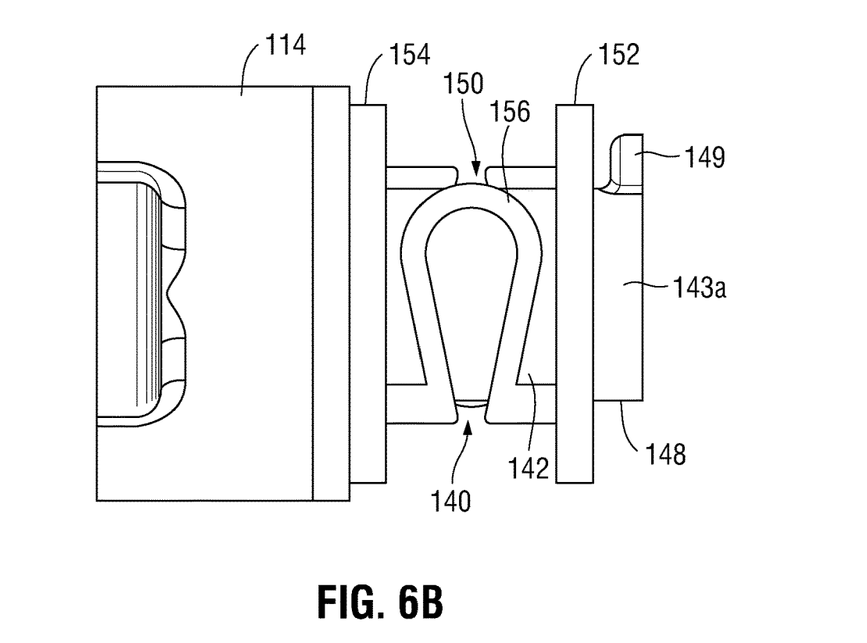
FIG. 6B is a side view of a proximal portion of the end effector assembly of the tissue resecting device of FIG. 1 illustrating the lock and release mechanism in the release condition.

With momentary reference to FIGS. 4, 5B, and 6B, upon engagement of end effector assembly 100 with handpiece assembly 200, as detailed below, proximal stop ring 152 is moved towards distal stop ring 154, and, as a result, biasing member 156 is compressed. This movement of proximal stop ring 152 is also relative to inner drive core 140, such that this movement of proximal stop ring 152 towards distal stop ring 154 displaces proximal stop ring 152 from about collar 148, thus displacing protrusion 149 from recess 153 and, in turn, releasing inner drive core 140 to permit rotation of inner cutting shaft 130 relative to elongated outer shaft 120.

Referring to FIGS. 1, 3, and 4, handpiece assembly 200 generally includes a handle housing 210, a drive assembly 220 disposed within handle housing 210, cable 230, and outflow tubing 240. Handle housing 210, as detailed above, is configured to releasably engage proximal hub housing 110 of end effector assembly 100, and defines a pistol-grip configuration, although other configurations are also contemplated. Handpiece assembly 200 may further include one or more controls (not shown) disposed on or operably associated with handle housing 210 to facilitate activation of drive assembly 220 in a desired manner.

Drive assembly 220 includes a distal drive rotor 222 and a motor 224 that drives rotation of distal drive rotor 222. Distal drive rotor 222 includes a plurality of splines (not explicitly shown, similar to splines 1226 of distal drive rotor 1222 (FIG. 7)) radially-spaced about the exterior thereof that are configured to mate with splines 146 of body 142 of inner drive core 140 of end effector assembly 100 upon engagement of end effector assembly 100 with handpiece assembly 200 to thereby engage distal drive rotor 222 and inner drive core 140 with one another. Cable 230 provides power and/or control signals to motor 224 to control rotation of distal drive rotor 222.

Outflow tubing 240 is configured such that, with end effector assembly 100 engaged with handle housing 210, outflow tubing 240 communicates with the internal lumen of inner cutting shaft 130 (see arrow "F" in FIG. 4) of end effector assembly 100 to receive resected tissue as well as fluid and other debris withdrawn from an internal surgical site during use. Outflow tubing 240 is configured to ultimately connect to a collection canister (not shown) or other suitable collection reservoir for collecting the tissue, fluid, and debris withdrawn from the internal surgical site.

Referring generally to FIGS. 2B, 3, 5A, and 6A, as noted above, prior to engagement of end effector assembly 100 with handpiece assembly 200, inner cutting shaft 130 is locked relative to elongated outer shaft 120 in a closed position (see FIG. 2B) via the bias of biasing member 156 retaining proximal stop ring 152 about collar 148 of inner drive core 140 with protrusion 149 of collar 148 received within recess 153.

In order to engage end effector assembly 100 with handpiece assembly 200, end effector assembly 100, lead by inner drive core 140, is inserted into handle housing 210 of handpiece assembly 200. With additional reference to FIGS. 4, 5B, and 6B, upon further insertion of end effector assembly 100 into handpiece assembly 200, inner drive core 140 is slid about distal drive rotor 222 such that the splines (not shown) of distal drive rotor 222 engage splines 146 of body 142 of inner drive core 140 to thereby rotatably engage distal drive rotor 222 and inner drive core 140 with one another.

As inner drive core 140 is slid about distal drive rotor 222 to engage distal drive rotor 222, proximal stop ring 152 is moved into contact with a shoulder 212 defined on the interior of handle housing 210 of handpiece assembly 200. Shoulder 212 inhibits further proximal movement of proximal stop ring 152 into handle housing 210 and, thus, as inner drive core 140 is slid further about distal drive rotor 222 to engage distal drive rotor 222, rather than proximal stop ring 152 advancing proximally therewith, proximal stop ring 152 remains stationary and biasing member 156 compresses to enable the continued proximal movement of inner drive core 140 (and distal stop ring 154) relative to proximal stop ring 152 until end effector assembly 100 is engaged with handpiece assembly 200.

The above-detailed proximal movement of inner drive core 140 (and distal stop ring 154) relative to proximal stop ring 152, enabled by the compression of biasing member 156, results in the displacement of proximal stop ring 152 from about collar 148, thus displacing protrusion 149 from recess 153. In this manner, lock and release mechanism 150 no longer constrains inner drive core 140; rather, inner drive core 140 is permitted to rotate, thus permitting rotation of inner cutting shaft 130 relative to elongated outer shaft 120. Accordingly, upon engagement of end effector assembly 100 and handpiece assembly 200, lock and release mechanism 150 releases inner drive core 140 and inner drive core 140 is engaged with distal drive rotor 222. Thus, with end effector assembly 100 engaged with handpiece assembly 200, motor 224 may be activated to drive rotation of distal drive rotor 222, thereby driving rotation of inner cutting shaft 130 relative to elongated outer shaft 120.

Once tissue resecting device 10 is assembled, e.g., once end effector assembly 100 is engaged with handpiece assembly 200 as detailed above, tissue resecting device is ready for use. In use, tissue resecting device 10 is positioned within an internal body cavity or organ, e.g., a uterus, such that the distal end portion of end effector assembly 100 is positioned adjacent tissue to be removed. Tissue resecting device 10 may be inserted through an endoscope, e.g., a hysteroscope, or other device, or may be used independently.

Once tissue resecting device 10 is positioned as desired adjacent tissue to be removed, tissue resecting device 10 is activated. Activation of tissue resecting device 10 drives motor 224 which rotationally drives drive rotor 222. Rotation of drive rotor 222, in turn, drives rotation of inner cutting shaft 130 relative to elongated outer shaft 120. Activation of tissue resecting device 10 also serves to activate suction through outflow tubing 240, thereby applying suction through inner cutting shaft 130. With such suction applied, tissue is drawn through window 128 of elongated outer shaft 120 and window 138 of inner cutting shaft 130, while edge 129 and/or cutting blade 139 facilitates cutting of tissue as a result of the rotation of windows 128, 138 relative to one another. The suction also draws fluid and debris through inner cutting shaft 130. The tissue, fluid, and debris suctioned through inner cutting shaft 130 travel proximally through inner cutting shaft 130, inflow tubing 240, and, ultimately, are deposited in a collection canister (not shown). Tissue resecting device 10 may be utilized until the desired tissue is removed from the internal body cavity or organ. Once the desired tissue is removed, tissue resecting device 10 may be deactivated and removed from the surgical site. Thereafter, end effector assembly 100 may be disengaged from handpiece assembly 200 and discarded (or sent for reprocessing), while handpiece assembly 200 is cleaned and/or sterilized for reuse.

Figure 7:
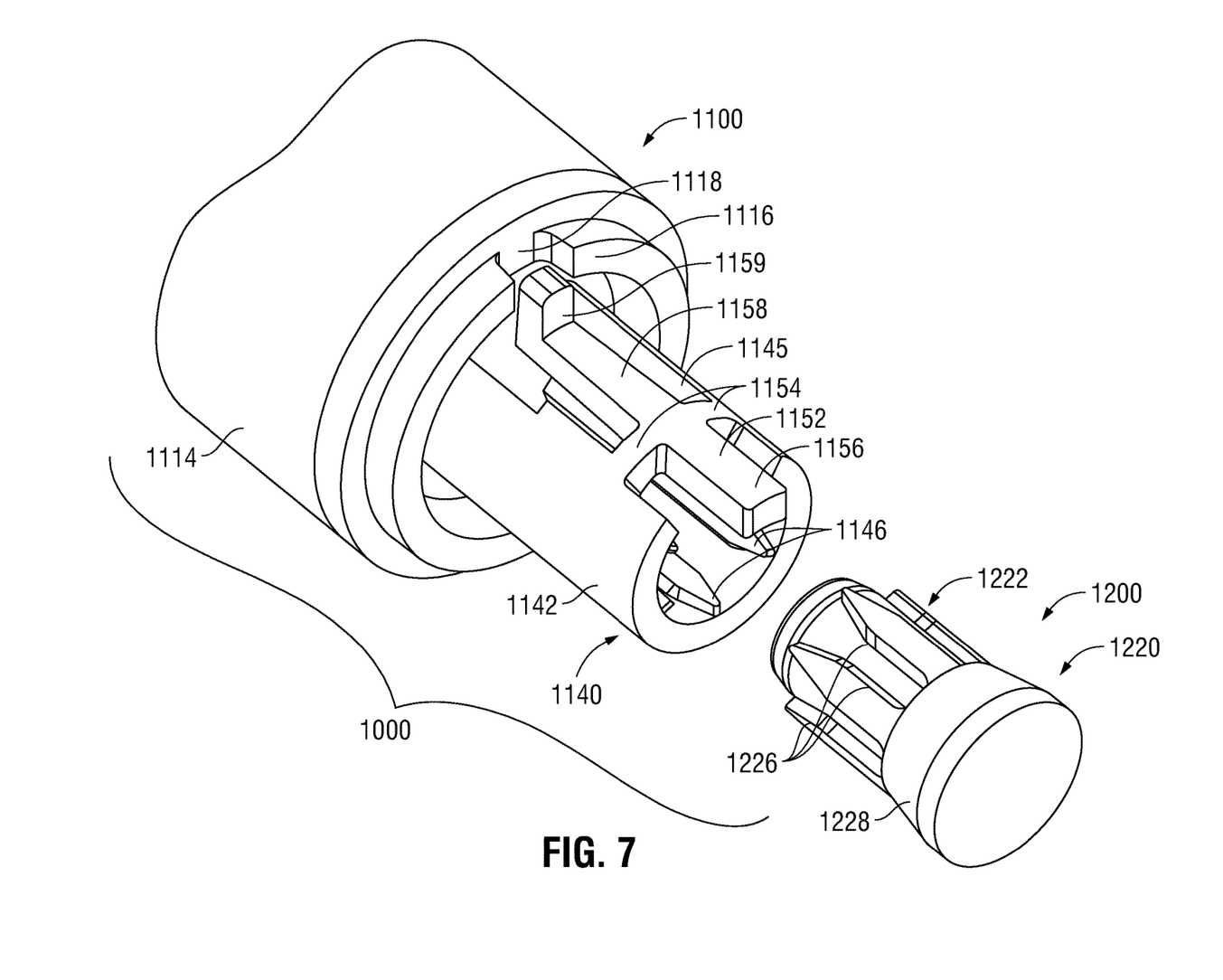
FIG. 7 is a perspective view illustrating another lock and release mechanism configured for use with the tissue resecting device of FIG. 1.

Referring to FIG. 7, another embodiment of a lock and release mechanism 1150 configured for use with a tissue resection device 1000 similar to tissue resection device 10 of FIGS. 1-6B (except as explicitly contradicted hereinbelow) is detailed. Lock and release mechanism 1150 includes a lock bar 1152 supported within a slot 1145 defined within body 1142 of inner drive core 1140 of end effector assembly 1100 via support arms 1154. Lock bar 1152 includes a proximal portion 1156 extending proximally from support arms 1154 and a distal portion 1158 extending distally from support arms 1154. Distal portion 1158 includes a protrusion 1159 extending therefrom. In an at-rest position of lock bar 1152, distal portion 1158 is positioned such that protrusion 1159 extends into a recess 1118 defined within a lock ring 1116 fixed relative to inner housing 1114 of end effector assembly 1100. As such, in the at-rest position of lock bar 1152, inner drive core 1140 is fixed relative to inner housing 1114 and, thus the inner cutting shaft (not explicitly shown, similar to inner cutting shaft 130 (FIGS. 1-2B)) is fixed relative to the elongated outer shaft (not explicitly shown, similar to elongated out shaft 110 (FIGS. 1-2B)). Inner drive core 1140 further includes a plurality of splines 1146 radially-spaced about the interior of a proximal portion of body 1142.

Continuing with reference to FIG. 7, distal drive rotor 1222 of drive assembly 1220 includes a plurality of splines 1226 formed on the exterior thereof and also includes a cam surface 1228 extending proximally from splines 1226. Cam surface 1228 may define, for example, a frustoconical configuration, or any other suitable configuration.

As noted above, in the at-rest position of lock bar 1152, e.g., prior to engagement of end effector assembly 1100 with handpiece assembly 1200, protrusion 1159 of distal portion 1158 of lock bar 1152 extends into recess 1118 of lock ring 1116 to fix inner drive core 1140 relative to inner housing 1114. In order to engage end effector assembly 1100 with handpiece assembly 1200, end effector assembly 1100, lead by inner drive core 1140, is inserted into the handle housing (not shown, similar to handle housing 210 (FIGS. 1, 3, and 4) of handpiece assembly 200). Upon such insertion, inner drive core 1140 is slid about distal drive rotor 1222 such that the splines 1226 of distal drive rotor 1222 engage splines 1146 of body 1142 of inner drive core 1140 to thereby rotatably engage distal drive rotor 1222 and inner drive core 1140 with one another.

As inner drive core 1140 is slid about distal drive rotor 1222 to engage distal drive rotor 1222, proximal portion 1156 of lock bar 1152 is moved into contact with cam surface 1228 of distal drive rotor 1222 and, upon further sliding of inner drive core 1140 about distal drive rotor 1222, proximal portion 1156 is urged radially outwardly from inner drive core 1140, e.g., due to the frustoconical (or other suitable) configuration of cam surface 1228. This radial outward urging of proximal portion 1156, in turn, pivots distal portion 1158 radially inwardly into inner drive core 1140, thus withdrawing protrusion 1159 of distal portion 1158 of lock bar 1152 from recess 1118 of lock ring 1116 and, as a result, releasing inner drive core 1140. Accordingly, upon engagement of end effector assembly 1100 and handpiece assembly 1200, lock and release mechanism 1150 releases inner drive core 1140 and inner drive core 1140 is engaged with distal drive rotor 1222.

As an alternative to handpiece assembly 200 (FIG. 1) and/or handpiece assembly 1200 (FIG. 7) configured for manual grasping and manipulation during use, tissue resecting devices 10, 1000 may alternatively be configured for use with a robotic surgical system wherein the end effector assembly 100, 1100 is configured to engage a robotic arm of the robotic surgical system in a similar manner as detailed above with respect to engagement of end effector assemblies 100, 11100 with handpiece assemblies 200, 1200, respectively. The robotic surgical system may employ various robotic elements to assist the surgeon and allow remote operation (or partial remote operation). More specifically, various robotic arms, gears, cams, pulleys, electric and mechanical motors, etc. may be employed for this purpose and may be designed with the robotic surgical system to assist the surgeon during the course of an operation or treatment. The robotic surgical system may include remotely steerable systems, automatically flexible surgical systems, remotely flexible surgical systems, remotely articulating surgical systems, wireless surgical systems, modular or selectively configurable remotely operated surgical systems, etc.

The robotic surgical system may be employed with one or more consoles that are next to the operating theater or located in a remote location. In this instance, one team of surgeons or nurses may prep the patient for surgery and configure the robotic surgical system with the surgical device disclosed herein while another surgeon (or group of surgeons) remotely control the surgical device via the robotic surgical system. As can be appreciated, a highly skilled surgeon may perform multiple operations in multiple locations without leaving his/her remote console which can be both economically advantageous and a benefit to the patient or a series of patients.

The robotic arms of the robotic surgical system are typically coupled to a pair of master handles by a controller. The handles can be moved by the surgeon to produce a corresponding movement of the working ends of any type of surgical instrument (e.g., end effectors, graspers, knifes, scissors, cameras, fluid delivery devices, etc.) which may complement the use of the tissue resecting devices described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A tissue resecting device, comprising:
   a handpiece assembly; and
   an end effector assembly configured to releasably engage the handpiece assembly, the end effector assembly including:
   a proximal hub housing;

an inner drive core at least partially disposed within the proximal hub housing;

a cutting member extending distally from the proximal hub housing and operably coupled with the inner drive core such that rotation of the inner drive core drives rotation of the cutting member; and a spring operably coupled between the inner drive core and the proximal hub housing and configured to releasably lock the inner drive core relative to the proximal hub housing, thereby rotationally locking the cutting member, wherein, in an extended position of the spring in the absence of engagement of the end effector assembly with the handpiece assembly, the cutting member is rotationally locked and wherein, in a compressed position of the spring with the end effector assembly engaged with the handpiece assembly, the cutting member is permitted to rotate, wherein, engagement of the end effector assembly with the handpiece assembly urges the spring to compress from the extended position to the compressed position to unlock the cutting member.

2. The tissue resecting device according to claim 1, wherein the spring is biased towards the extended position.

3. The tissue resecting device according to claim 1, wherein the spring is configured to expand and compress along a longitudinal axis of the inner drive core.

4. The tissue resecting device according to claim 1, wherein the spring is disposed about a portion of the inner drive core.

5. The tissue resecting device according to claim 1, further comprising an elongated outer shaft fixed relative to and extending distally from the proximal hub housing, wherein the cutting member is received within the elongated outer shaft, rotationally fixed relative to the elongated outer shaft when rotationally locked, and rotatable relative to the elongated outer shaft when permitted to rotate.

6. The tissue resecting device according to claim 1, wherein a portion of the handpiece assembly urges the spring to compress from the extended position towards the compressed position.

7. The tissue resecting device according to claim 1, further comprising a first stop ring disposed at a first end of the spring and a second stop ring disposed at a second end of the spring, wherein the first stop ring, the second stop ring, and the spring are integrally formed as a single piece of material.

8. The tissue resecting device according to claim 1, wherein the inner drive core includes a proximal end portion configured to operably couple to a drive rotor of the handpiece assembly when the end effector assembly is engaged with the handpiece assembly.

9. The tissue resecting device according to claim 8, wherein the proximal end portion defines a lumen and includes at least one spline extending into the lumen, the at least one spline configured to engage the drive rotor.

10. The tissue resecting device according to claim 1, wherein the engagement of the end effector assembly with the handpiece assembly maintains the spring in the compressed position thereby maintaining the cutting member unlocked.

\* \* \* \* \*